US010398807B2

(12) United States Patent
Mintz et al.

(10) Patent No.: US 10,398,807 B2
(45) Date of Patent: Sep. 3, 2019

(54) CANISTER LID AND CORRESPONDING SYSTEMS AND METHODS

(71) Applicant: Medline Industries, Inc., Mundelein, IL (US)

(72) Inventors: Stuart Mintz, Glenview, IL (US); Derek Roberts, Chicago, IL (US); Brian Barkeley, Chicago, IL (US)

(73) Assignee: Medline Industries, Inc., Northfield, IL (US)

( * ) Notice: Subject to any disclaimer, the term of this patent is extended or adjusted under 35 U.S.C. 154(b) by 355 days.

(21) Appl. No.: 15/005,741

(22) Filed: Jan. 25, 2016

(65) Prior Publication Data
US 2017/0209628 A1  Jul. 27, 2017

(51) Int. Cl.
*A61M 1/00* (2006.01)
(52) U.S. Cl.
CPC ........ *A61M 1/0003* (2013.01); *A61M 1/0001* (2013.01); *A61M 1/005* (2014.02); *A61M 1/0017* (2014.02)
(58) Field of Classification Search
CPC .. A61M 1/0003; A61M 1/0017; A61M 1/005; A61M 1/0001
See application file for complete search history.

(56) References Cited

U.S. PATENT DOCUMENTS

| | | |
|---|---|---|
| 3,814,098 A | 6/1974 | Deaton |
| 3,866,608 A | 2/1975 | Reynolds et al. |
| 4,321,922 A | 3/1982 | Deadon |
| 4,379,455 A | 4/1983 | Deaton |
| 4,419,093 A | 12/1983 | Deaton |
| 4,430,084 A | 2/1984 | Deaton |
| 4,460,361 A | 7/1984 | Nichols |
| 4,681,571 A | 7/1987 | Nehring |
| 4,802,506 A | 2/1989 | Aslanian |
| 5,185,007 A | 2/1993 | Middaugh et al. |
| 5,234,419 A | 8/1993 | Bryant et al. |

(Continued)

FOREIGN PATENT DOCUMENTS

| | | |
|---|---|---|
| AU | 649128 | 5/1994 |
| CN | 201353366 | 12/2009 |

(Continued)

OTHER PUBLICATIONS

*Medi-Vac Suction and Fluid Collection Products*; Flex Advantage Suction Canister System; Publication; Cardinal Health; Unknown publication date prior to filing of present application.

(Continued)

*Primary Examiner* — Kai H Weng
(74) *Attorney, Agent, or Firm* — Philip H. Burrus, IV

(57) ABSTRACT

A canister lid (100) for a canister (600) includes an annular perimeter (101) surrounding an interior portion (102). Rather than completely surrounding the interior portion, the annular perimeter is instead interrupted by a suction conduit (103) defined by a suction duct (104) separating a first lobe (105) and a second lobe (106). The suction duct (104) intersects the annular perimeter such that the first lobe is disposed interior of the annular perimeter while the second lobe is disposed exterior to the annular perimeter. The canister lid can further include one or more ports (110,111) extending from the interior portion.

18 Claims, 7 Drawing Sheets

(56) References Cited

U.S. PATENT DOCUMENTS

| | | | |
|---|---|---|---|
| 5,279,602 | A | 1/1994 | Middaugh et al. |
| 5,470,324 | A | 11/1995 | Cook et al. |
| 5,624,417 | A | 4/1997 | Cook et al. |
| 5,725,516 | A | 3/1998 | Cook et al. |
| 5,792,126 | A | 8/1998 | Tribastone et al. |
| 5,944,703 | A | 8/1999 | Dixon et al. |
| 6,053,896 | A | 4/2000 | Wilson et al. |
| 6,056,731 | A | 5/2000 | Koetke et al. |
| 6,071,095 | A | 6/2000 | Verkaat |
| 6,093,230 | A | 7/2000 | Johnson, III et al. |
| 6,342,048 | B1 | 1/2002 | Verkaart et al. |
| 6,575,946 | B2 | 6/2003 | Sealfon |
| 6,626,877 | B2 | 9/2003 | Anderson et al. |
| 6,652,495 | B1 | 11/2003 | Walker |
| 6,663,586 | B2 | 12/2003 | Verkaart et al. |
| 6,672,477 | B2 | 1/2004 | Miller et al. |
| 6,673,055 | B2 | 1/2004 | Bemis et al. |
| 6,780,309 | B2 | 8/2004 | Haldopoulos et al. |
| 7,115,115 | B2 | 10/2006 | Bemis et al. |
| 7,153,294 | B1 | 12/2006 | Farrow |
| 7,481,243 | B2 | 1/2009 | Michaels et al. |
| 7,585,292 | B2 | 9/2009 | Anderson et al. |
| 7,674,248 | B2 | 3/2010 | Anderson et al. |
| 7,806,879 | B2 | 10/2010 | Brooks et al. |
| 8,118,796 | B2 | 2/2012 | Rajamaki |
| 8,715,255 | B2 | 5/2014 | Christen |
| 2005/0139532 | A1 | 6/2005 | Hershberger et al. |
| 2007/0016152 | A1* | 1/2007 | Karpowicz ......... A61M 1/0001 604/326 |
| 2008/0004574 | A1 | 1/2008 | Dyar et al. |
| 2009/0030384 | A1 | 1/2009 | Christen et al. |
| 2009/0247968 | A1* | 10/2009 | Brooks ............... A61M 1/0001 604/319 |
| 2014/0236129 | A1 | 8/2014 | Radl et al. |
| 2015/0141943 | A1 | 5/2015 | Koch et al. |

FOREIGN PATENT DOCUMENTS

| | | |
|---|---|---|
| DE | 102008027486 | 12/2009 |
| EP | 0466884 | 5/1996 |
| EP | 0659090 | 2/1999 |
| EP | 0830152 | 5/2003 |
| EP | 983098 | 10/2004 |
| EP | 831943 | 12/2004 |
| EP | 858347 | 3/2005 |
| EP | 1225930 | 11/2006 |
| FR | 2639543 | 11/1988 |
| JP | 04077517 | 4/2008 |
| WO | WO-92014496 | 9/1992 |
| WO | WO-9414045 | 6/1994 |
| WO | WO-96011031 | 4/1996 |
| WO | WO-97000090 | 1/1997 |
| WO | WO-9714450 | 4/1997 |
| WO | WO-9855164 | 12/1998 |
| WO | WO-01072350 | 10/2001 |
| WO | WO-2005025666 | 3/2005 |
| WO | 2008/144951 | 12/2008 |
| WO | WO-2015055893 | 4/2015 |
| WO | WO-01024846 | 1/2016 |

OTHER PUBLICATIONS

*Medi-Vac Suction and Fluid Collection Products Catalog*; CRD Hardware; Cardinal Health; Copyright 20013; Unknown Publication date but prior to filing of present application.

Weng, Kai , "NonFinal OA", U.S. Appl. No. 15/214,280, filed Jul. 19, 2016, dated Mar. 29, 2019.

Weng, Kai , "NonFinal OA", U.S. Appl. No. 15/437,232, filed Feb. 20, 2017, dated Mar. 4, 2019.

* cited by examiner

CANISTER LID AND CORRESPONDING SYSTEMS AND METHODS

BACKGROUND

Technical Field

This disclosure relates generally to canister lids, and more particularly to suction canister lids.

Background Art

Medical professionals, such as surgeons, use vacuum-like devices to remove excess fluids during medical procedures. For example, during a surgical procedure, a surgeon will couple a suction device to a fluid collection canister by way of a flexible tube. The suction device draws unwanted fluids from the surgical site into the canister. A coagulant can then be added to the fluid to transform it to a solid or semi-solid for disposal. Fluid collection canisters are used to collect and dispose of fluids in a variety of medical procedures.

Fluid collection canisters have evolved over the years. In the early twentieth century, fluid collection canisters were manufactured from glass. After a particular procedure, the glass canister was sterilized and reused. Sometime around the 1960's, plastic fluid collection canisters, such as those manufactured from polystyrene, began to replace glass canisters. The polystyrene canisters were disposable, thereby reducing the chance of a patient getting an infection or other malady as a result of improper sterilization.

In the 1990's, to combat the large amount of waste associated with discarding entire fluid collection canisters, liners were introduced. Rather than capturing fluid in the canister itself, fluids were captured in a disposable lining. The introduction of liners reduced both cost and the amount of waste.

Regardless of the type of canister used, little has changed in how the canister operates. This is particularly true when it comes to the design of the lid. With traditional suction canister systems, hoses are connected to ports disposed along the top of the lid. Commonly assigned U.S. patent application Ser. No. 12/769,900, filed Apr. 29, 2010, which is incorporated herein by reference, teaches a lid member having an interior portion and a perimeter portion, with a plurality of ports extending from the interior portion. Tubes can be coupled to these ports in a fluid collection application.

While such systems work well in practice, the various tubings connected to the ports of the lid can become tangled and can be ensnared by other objects. It would be advantageously to have an improved canister lid suitable for use with fluid collection canisters.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
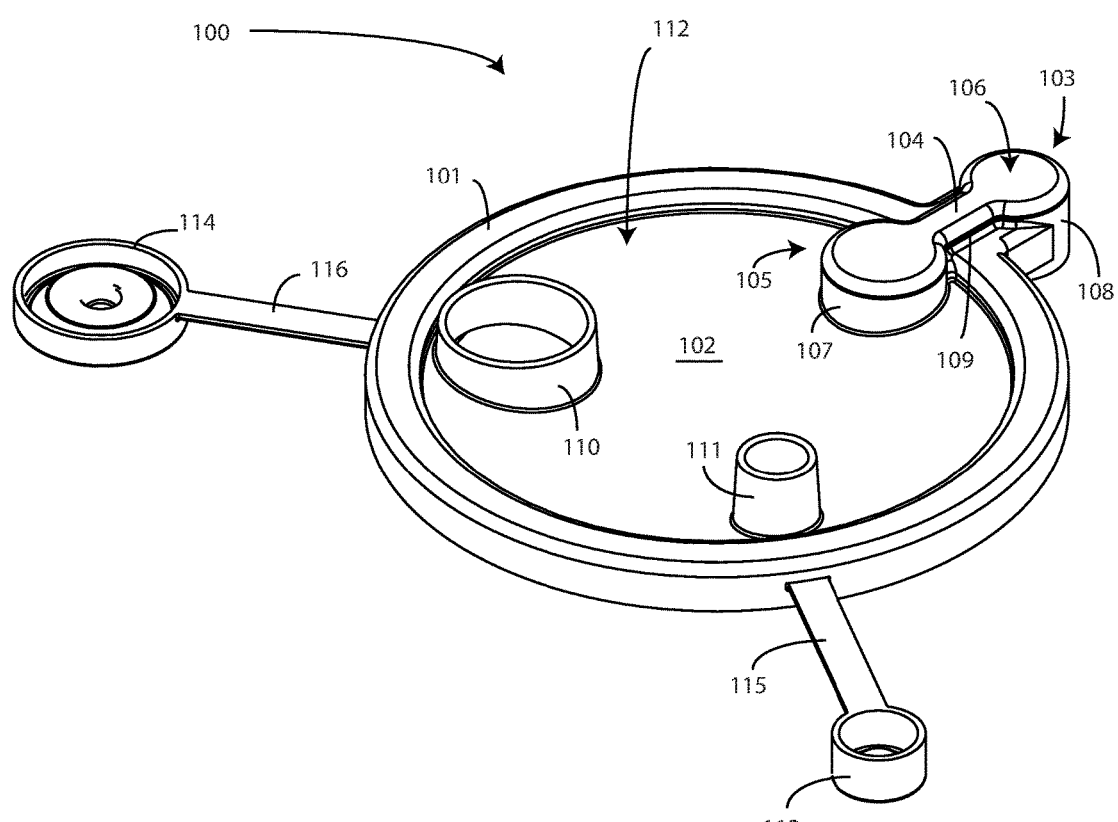
FIG. 1 illustrates a perspective view of one explanatory canister lid in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A. The apparatus components shown below have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Embodiments of the disclosure provide a canister lid that is suitable for use with a canister in fluid collection operations. Advantageously, canister lids configured in accordance with embodiments of the disclosure eliminate one or more of the tubes or hoses required with prior art systems. Not only does this reduce system complexity and cost, the elimination of a hose or tube makes use of fluid collection canisters equipped with canister lids configured in accordance with embodiments of the disclosure quicker and less complex as well.

In one embodiment, a canister lid includes an annular perimeter surrounding an interior portion, which may be planar, convex, or concave. Instead of including a suction port and an exhaust port along the interior portion, in one embodiment the canister lid includes a suction conduit extending from a perimeter of the canister lid. In one embodiment, the suction conduit interrupts the annular perimeter with a portion of the suction duct that extends distally away from the annular perimeter.

In one or more embodiments, the suction conduit includes a suction duct that separates a first lobe and a second lobe. In one or more embodiments, the first lobe and the second lobe are substantially circular, while the suction duct is substantially straight. Accordingly, in such an embodiment when the suction conduit is viewed in plan view, the suction conduit can resemble a dog bone or double-ended lollipop.

In one or more embodiments, the suction duct separates the first lobe and the second lobe and traverses or intersects the annular perimeter such that the first lobe is disposed interior of the annular perimeter while the second lobe is disposed exterior to the annular perimeter. In one embodiment, the second lobe is operable to engage a suction port extending distally from the sidewall of a canister when the annular perimeter engages the lip of the canister. Advantageously, air can flow from the second lobe through the suction duct to the first lobe, or vice versa, such that the suction conduit serves as either a suction input or an exhaust. This eliminates the need for at least one tube or hose in fluid collection operations.

Figure 2:
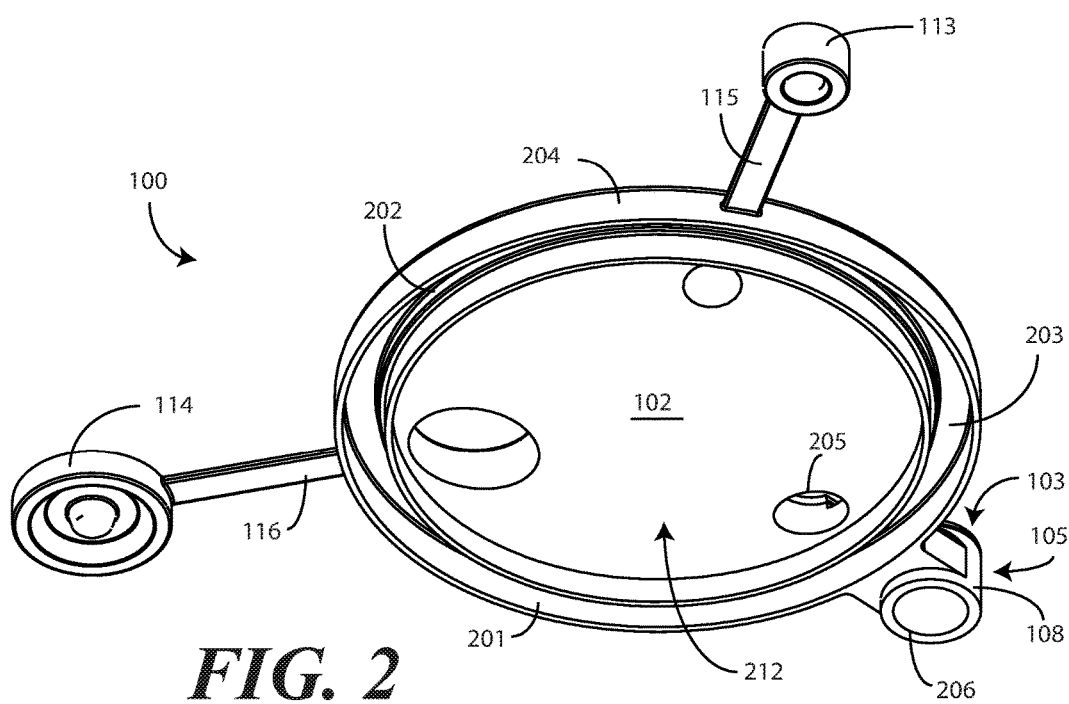
FIG. 2 illustrates another perspective view of one explanatory canister lid in accordance with one or more embodiments of the disclosure.
Figure 3:
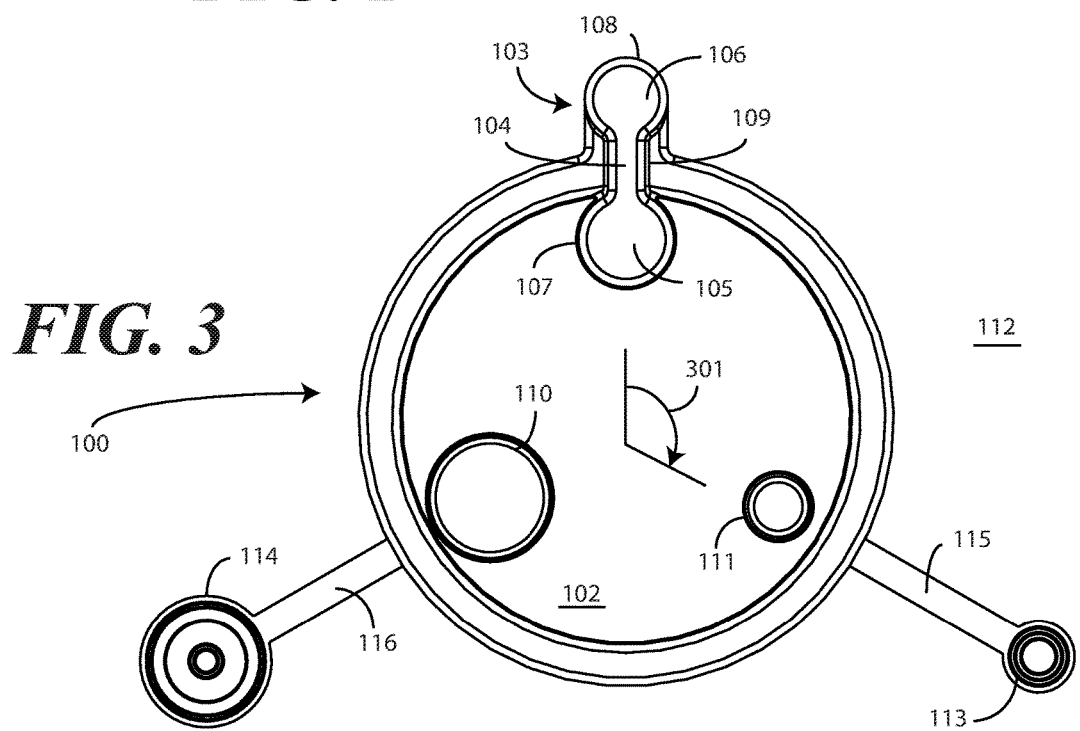
FIG. 3 illustrates a top plan view of one explanatory canister lid in accordance with one or more embodiments of the disclosure.
Figure 4:
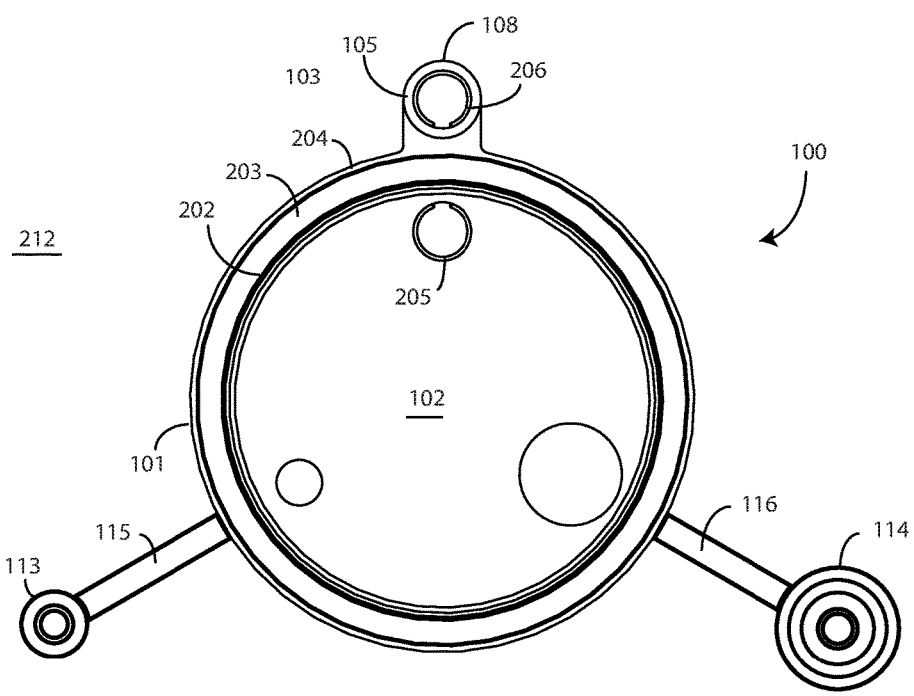
FIG. 4 illustrates a bottom plan view of one explanatory canister lid in accordance with one or more embodiments of the disclosure.
Figure 5:
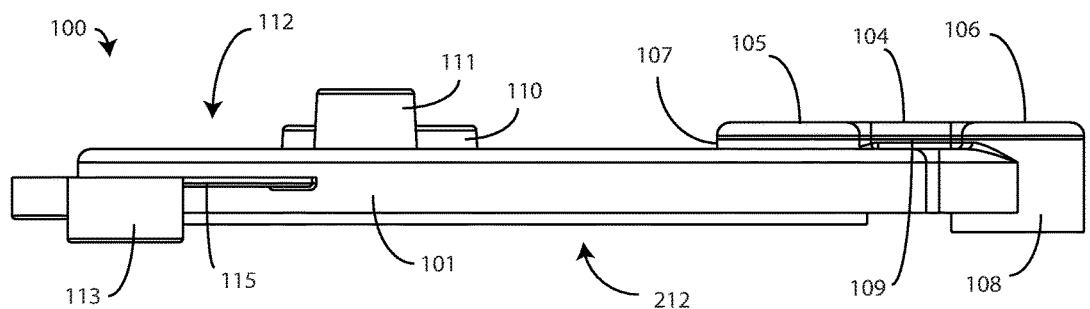
FIG. 5 illustrates a side elevation view of one explanatory canister lid in accordance with one or more embodiments of the disclosure.

Turning now to FIGS. 1-5, illustrated therein is one embodiment of a canister lid 100 configured in accordance with one or more embodiments of the disclosure. FIG. 1 illustrates a top perspective view of the canister lid 100, while FIG. 2 illustrates a bottom perspective view of the canister lid 100. FIG. 3 illustrates a top plan view of the canister lid 100, while FIG. 4 illustrates a bottom plan view of the canister lid 100. FIG. 5 illustrates a side elevation view of the canister lid 100.

In one or more embodiments, the canister lid 100 can be manufactured from a thermoplastic material by way of an injection molding process. For example, in one embodiment, the canister lid 100 is manufactured from polypropylene. In another embodiment, the canister lid 100 is manufactured from polyethylene. It will be obvious to those of ordinary skill in the art having the benefit of this disclosure that other suitable semi-rigid materials may be substituted for the thermoplastic. Further, other manufacturing processes may be used to fabricate the canister lid 100 as well.

In the illustrative embodiment of FIGS. 1-5, the canister lid 100 includes an annular perimeter 101 surrounding an interior portion 102. In one embodiment, the annular perimeter 101 defines a substantially circular (when viewed in plan view) sidewall surrounding the interior portion 102. In one or more embodiments, the annular perimeter 101 is operable as a "canister connector" in that it is configured to connect to a canister, one example of which is a fluid collection canister.

In one embodiment, the canister lid 100 also includes a suction conduit 103. As shown in FIG. 1-5, in one embodiment the suction conduit 103 comprises a suction duct 104, a first lobe 105, and a second lobe 106. In this illustrative embodiment, rather than completely surrounding the interior portion 102, the suction conduit 103 instead interrupts the annular perimeter 101. As best shown in FIG. 3, in one embodiment the suction duct 104 separating the first lobe 105 and the second lobe 106 traverses or intersects the annular perimeter 101 such that the first lobe 105 is disposed interior of the annular perimeter 101 along the interior portion 102 of the canister lid 100, while the second lobe 106 is disposed exterior to, and extends distally away from an outer edge of, the annular perimeter 101.

In one or more embodiments, the first lobe 105 and the second lobe 106 are substantially circular, while the suction duct 104 is substantially straight. Accordingly, in such an embodiment when the suction conduit is viewed in plan view, the suction conduit can resemble a dog bone or double-ended lollipop. In colloquial terms, in one embodiment the center of the "dog bone" of the suction conduit 103 bisects the annular perimeter 101 with half of the dog bone, i.e., the second lobe 106 and a portion of the suction duct 104, extending outwardly away from an outer side of the annular perimeter 101 while another half of the dog bone, i.e., the first lobe 105 and another portion of the suction duct 104, are inside the annular perimeter 101 and traverse the interior portion 102 of the canister lid 100.

In one or more embodiments, the suction conduit 103 is hollow on the inside such that air or other fluid can be drawn through each of the first lobe 105, the suction duct 104, and the second lobe 106. Illustrating by example, as best seen in FIGS. 2 and 4, the bottom side of the canister lid 100 includes a first aperture 205 disposed under the first lobe 105. There is also a second aperture 206 disposed under the second lobe 106. Accordingly, the first lobe 105 and the second lobe 106 serve as chamber walls for the first aperture 205 and the second aperture 206, respectively. As the suction duct 104 is hollow and connects these two chambers, air and other fluids can flow into the first aperture 205, through the first lobe 105, through the suction duct 104, into the second lobe 106, and out of the second aperture 206, or vice versa. Thus, the inclusion of the suction conduit 103 advantageously allows for the elimination of a hose that would traditionally be used to remove air from, or deliver air to, a suction canister.

In one embodiment, the first lobe 105 comprises a first lobe annular wall 107. Similarly, in one embodiment the second lobe 106 comprises a second lobe annular wall 108. The suction duct 104 can include one or more suction duct sidewalls 109 that connect the first lobe annular wall 107 and the second lobe annular wall 108. As best shown in FIG. 3, in this illustrative embodiment the first lobe annular wall 107 and the second lobe annular wall 108 are substantially circular in cross section. However, it should be noted that other shapes can be substituted for the generally circular first lobe annular wall 107 and second lobe annular wall 108. These sidewalls could alternatively be rectangular, triangular, take free form shapes, or be ovular, pentagonal, hexagonal, and so forth. Other shapes and configurations for the first lobe annular wall 107 and the second lobe annular wall 108 will be obvious to those of ordinary skill in the art having the benefit of this disclosure.

In this illustrative embodiment, as best seen in FIG. 3, the first lobe annular wall 107 is greater in circumference than is the second lobe annular wall 108. This results in the first lobe 105 being a "bigger circle" or "bigger end of the dog bone" than the second lobe 106. In other embodiments, the second lobe annular wall 108 may have a greater perimeter than the first lobe annular wall 107. In still other embodiments, the first lobe annular wall 107 and the second lobe annular wall 108 will have substantially equal perimeters.

In one or more embodiments, the annular perimeter 101 of the canister lid 100 is operable to connect to the lip edge of a canister. When this occurs, the interior portion 102 spans and essentially seals the opening of the canister. Embodiments of the canister will be shown in subsequent figures. In one or more embodiments, the canister lid 100 also includes one or more ports 110,111 extending from the interior portion 102. The one or more ports 110,111 facilitate the transport of fluids, be they air, liquids, or other fluids, into and away from the canister. In this illustrative embodiment, the canister lid 100 includes two ports 110,111.

For reference, the canister lid 100 can be thought of as having a top side 112 and a "canister engaging side" 212. The top side 112 is shown in plan view in FIG. 3, while the canister engaging side 212 is shown in plan view in FIG. 4. For convention, the top side 112 is the side exposed to the environment when the canister lid 100 is coupled to a canister. By contrast, the canister engaging side 212 engages the canister and correspondingly is oriented toward the interior of the canister when the canister lid 100 seals the canister. In the illustrative embodiment of FIGS. 1-5, each of the ports 110,111 extends distally from the interior portion 102 from the top side 112. By contrast, the first aperture 205 disposed beneath the first lobe 105 and the second aperture 206 disposed beneath the second lobe 106 are each disposed on the canister engaging side 212.

As noted above, in one or more embodiments the one or more ports 110,111 facilitate fluid collection and transport to and from a canister to which the canister lid 100 is coupled. While the ports can be arranged in any number of ways, and can accommodate any number of functions, in one embodiment a first port 111 comprises a suction port while a second port 110 comprises a pour spout.

In one or more embodiments, a tube or hose can be coupled to the suction port. A vacuum or other suction appliance is then coupled to the second aperture 206 disposed beneath the second lobe 106. The tube or hose coupled to the suction port can then coupled to a hand-held suction device. When the vacuum or suction appliance is actuated, the vacuum draws air from the canister through the first aperture 205 disposed beneath the first lobe 105, through the suction duct 104, through the second lobe 106 and out the second aperture 206. This causes fluid to be drawn through the hand-held suction device into the suction port and into the canister to which the canister lid 100 is coupled. Fluid can be prevented from entering the vacuum or suction device by way of a filter (not shown) placed beneath the first aperture 205 disposed beneath the first lobe 105.

In other embodiments, the suction port can alternatively be used as a tandem port. A tandem port is a port that can be used to daisy chain fluid collection canisters together. For example, in some medical procedures, it will be anticipated that more fluid will be collected than can be stored in a single fluid collection canister. In such situations, it may be necessary to couple multiple fluid collection canisters together with a tandem port, such that when one gets full, fluid can be delivered to other, empty fluid collection canisters.

The pour spout can be used for a variety of purposes. Illustrating by example, in one or more embodiments the pour spout can be used for pouring solidifier into a filled canister after drawing fluids into the canister. The solidifier agglutinates the fluid, thereby making it easy to transport or dispose. In alternate embodiments, the pour spout can be used to pour fluids out of the canister.

In one or more embodiments, such as for optimum draw when in operation, ports not in use can be sealed with one or more caps 113,114 that are integrally tethered, in this illustrative embodiment, to the canister lid 100 by a corresponding tab 115,116. Illustrating by example, if fluids were being drawn into the suction port, cap 114 could be placed atop the pour spout to seal it. Conversely, if liquid was being poured out the pour spout, cap 113 could be placed over the suction port. Where fluids were being transported, cap 114 could be placed over the pour spout while cap 113 was placed over the suction port. In one or more embodiments, the one or more caps 113,114 are to cover the one or more ports 110,111 on a one-to-one basis.

In one or more embodiments, to prevent the caps from being lost, each cap 113,114 is tethered directly to an exterior wall of the annular perimeter 101 by a corresponding tab 115,116 that is integrally formed with, and extends distally away from, the exterior wall of the annular perimeter 101. In this illustrative embodiment, each tab 115,116 extends substantially orthogonally away from the exterior wall of the annular perimeter 101.

While the one or more ports 110,111 can be disposed in various locations across the interior portion 102 of the canister lid 100, in one embodiment the ports 110,111 and the first lobe 105 of the suction conduit 103 are roughly evenly spaced around the interior portion 102. For example, as best seen in FIG. 3, in one embodiment the first lobe 105, the pour spout, i.e., port 110, and the suction port, i.e., port 111, are each radially separated 301 by about 120 degrees along the interior portion 102. This results in the first lobe 105 being roughly at the "twelve o'clock" position when the suction conduit 103 is oriented at the top of the canister lid 100, while port 111 is roughly at the four o'clock position and port 110 is roughly at the eight o'clock position. Arranging the first lobe 105 and one or more ports 110,111 in this orientation offers maximum separation from each element about the interior portion 102 of the canister lid 100.

In this illustrative embodiment, the one or more ports 110,111 extend distally from the top side 112 of the interior portion 102 of the canister lid 100. In one embodiment, each of the one or more ports 110,111 extends to a common height from the interior portion 102 of the canister lid 100. However, in other embodiments, to provide a mnemonic device indicating which port 110,111 is used for which function, the one or more ports 110,111 extend to different heights from the interior portion 102 of the canister lid. For instance, in this illustrative embodiment, as best shown in FIG. 5, port 111 extends distally away from the interior portion 102 farther than does port 110. Accordingly, where port 111 is a suction port and port 110 is a pour spout, port 111 can extend farther from the interior portion 102 to facilitate the connection of a hose or tube for suction operations.

In one or more embodiments, as best shown in FIGS. 2 and 4, the annular perimeter 101 defines a canister lip engaging recess 201 open to the canister engaging side 212 of the canister lid 100. In one or more embodiments, the canister lip engaging recess 201 comprises a first annular wall 202, a second annular wall 204, and a bridge 203 spanning the first annular wall 202 and the second annular wall 204. In this illustrative embodiment, the second annular wall 204 comprises an exterior wall of both the canister lid 100 and the annular perimeter 101. In one or more embodiments, the bridge 203 is oriented substantially orthogonally with both the first annular wall 202 and the second annular wall 204.

In one or more embodiments, the canister lip engaging recess 201 can include mechanical features for engaging the lip edge of a canister. Examples of these mechanical features include mechanical locks, snaps, and the like. In other embodiments, the canister lip engaging recess 201 can include threads so as to be screwed onto a canister to form a hermetic seal. In such an embodiment, the second annular wall 204 can include an inclined plane disposed along an interior portion of the second annular wall 204 that defines a thread. Alternatively, a dual thread can be used. Other attachment mechanisms suitable for use in the canister lip engaging recess 201 will be obvious to those of ordinary skill in the art having the benefit of this disclosure.

In the illustrative embodiment of FIGS. 1-5, each of the one or more of ports 110,111 extends distally from the interior portion 102 by a height that exceeds a height of the annular perimeter 101. Said differently, in one or more embodiments a height of the first annular wall 202 to the top side 112 from the interior portion 102 is less than a height of either of the one or more ports 110,111 as best shown in FIG. 5.

Figure 6:
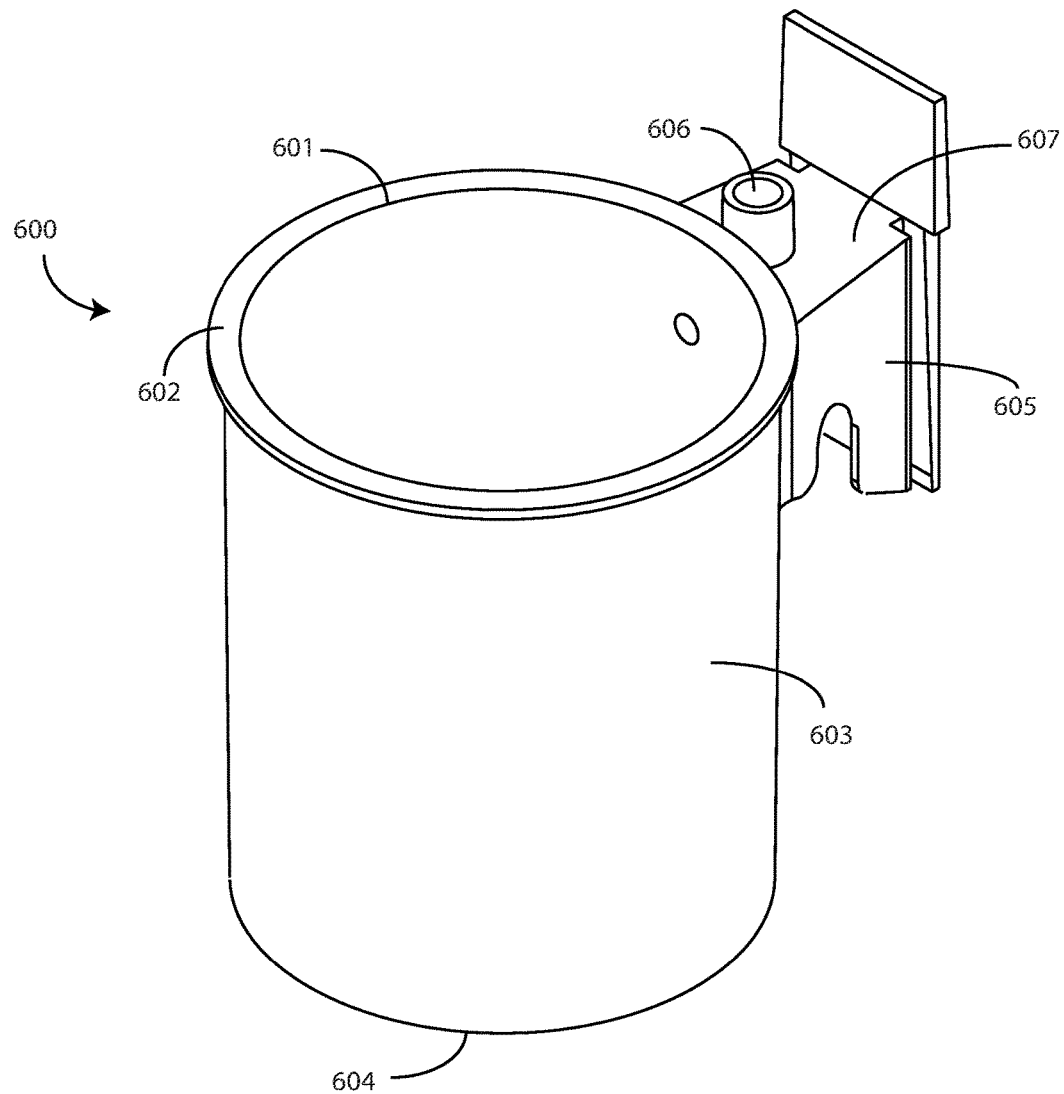
FIG. 6 illustrates one explanatory canister suitable for use with an explanatory canister lid in accordance with one or more embodiments of the disclosure.

Turning now to FIG. 6, illustrated therein is one illustrative canister 600 suitable for use with a canister lid (100) configured in accordance with one or more embodiments of the disclosure. Canisters suitable for use with embodiments of the disclosure can be manufactured in different sizes. For example, in one embodiment the canister 600 is a 2400 cc canister. In another embodiment, the canister 600 is a 1500 cc canister. These sizes are exemplary only, and embodiments of the invention are not intended to be limited in this regard, as any of canisters suitable for use with the invention can be created in a wide variety of sizes.

In one embodiment, the canister 600 is manufactured from a clear, substantially rigid thermoplastic by way of an injection molding process. For example, in one embodiment the canister 600 is manufactured from clear polystyrene, which is also known sometimes by the name "crystal styrene."

In one embodiment, the canister includes a rim 601, which may include a lip 602 or other mating feature that is suitable for coupling to or otherwise engaging a canister lip engaging recess (201) of a canister lid (100). In this illustrative embodiment, the canister includes a cylindrical sidewall 603 that extends from a base 604. In this illustrative embodiment, the cylindrical sidewall 603 is substantially orthogonal relative to the base 604. However, in other embodiments, the cylindrical sidewall 603 is modestly tapered, such as by two degrees. In still other embodiments, the canister 600 can include tapered sidewalls that extend distally from the base 604 to the rim 601 with an outward flare. Tapered sidewalls help facilitate release of the canister 600 both from stacked configurations with other canisters and from a mold, where the canister 600 can be manufactured by injection molding. In one or more embodiments, the lip 602 extends outwardly from the cylindrical sidewall 603.

In this illustrative embodiment, the canister 600 also includes an exterior suction assembly 605. The exterior suction assembly includes a suction port 606 extending distally from the cylindrical sidewall 603 on a mechanical support 607 that allows the suction port 606 to attach to a central vacuum or suction apparatus in a hospital or other medical facility. Advantageously, the "overhanging dog bone" of the second lobe (106) extending from the annular perimeter (101) of a canister lid (100) configured in accordance with one or more embodiments of the disclosure allows this suction port 606 to draw air through the suction conduit (103) from the interior 608 of the canister 600. To provide this functionality, the second lobe (106) is to engage the suction port 606 when the canister lip engaging recess (201) of the annular perimeter (101) of a canister lid (100) engages the lip 602 of the canister 600. This will be shown in more detail in FIG. 9 below.

Figure 7:
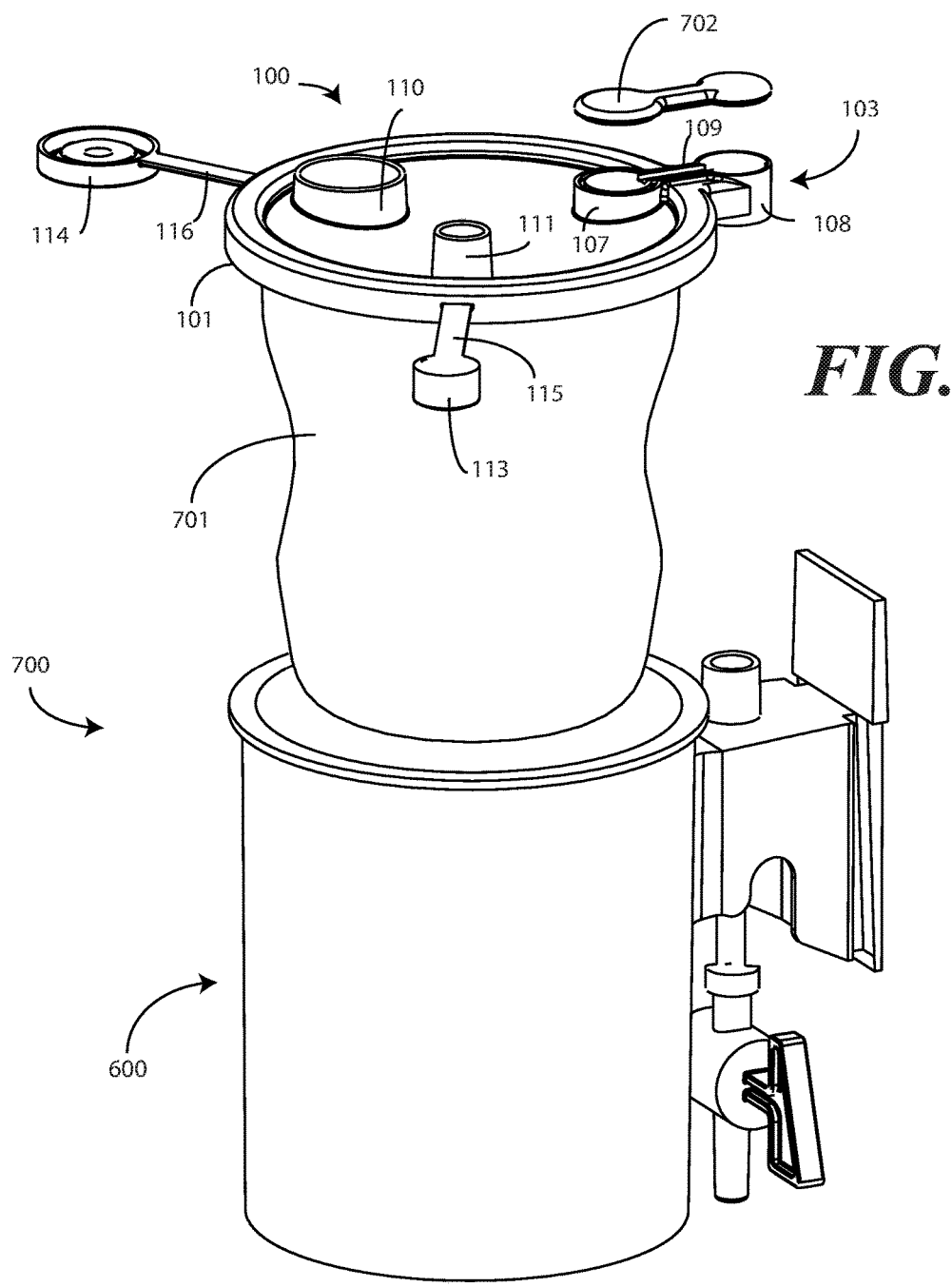
FIG. 7 illustrates an exploded view of one explanatory canister system in accordance with one or more embodiments of the disclosure.

Turning now to FIG. 7, illustrated therein is a canister system 700 configured in accordance with one or more embodiments of the disclosure. The canister system 700 includes the canister lid 100 of FIGS. 1-5 and the canister 600 of FIG. 6. Attached to the canister lid 100 in this embodiment is a disposable liner 701 operable to catch fluids or other materials drawn in through the suction port.

In one or more embodiments, the canister lid 100 is manufactured as a unitary, singular, integrated part where, for example, the annular perimeter 101, interior portion 102, ports 110,111, suction conduit 103, caps 113,114, and tabs 115,116 comprise a single part. However, in the illustrative embodiment of FIG. 7, the suction conduit 103 comprises a separate suction conduit cap 702 coupled to each of the first lobe annular wall 107, the second lobe annular wall 108, and the one or more suction duct sidewalls 109. The suction conduit cap 702 can be adhesively sealed to each of the first lobe annular wall 107, the second lobe annular wall 108, and the one or more suction duct sidewalls 109 in one embodiment. Alternatively, the suction conduit cap 702 can be thermally or ultrasonically welded to each of the first lobe annular wall 107, the second lobe annular wall 108, and the one or more suction duct sidewalls 109 in other embodiments. Other manufacturing processes for adhering the suction conduit cap 702 to each of the each of the first lobe annular wall 107, the second lobe annular wall 108, and the one or more suction duct sidewalls 109 will be obvious to those of ordinary skill in the art having the benefit of this disclosure.

Figure 8:
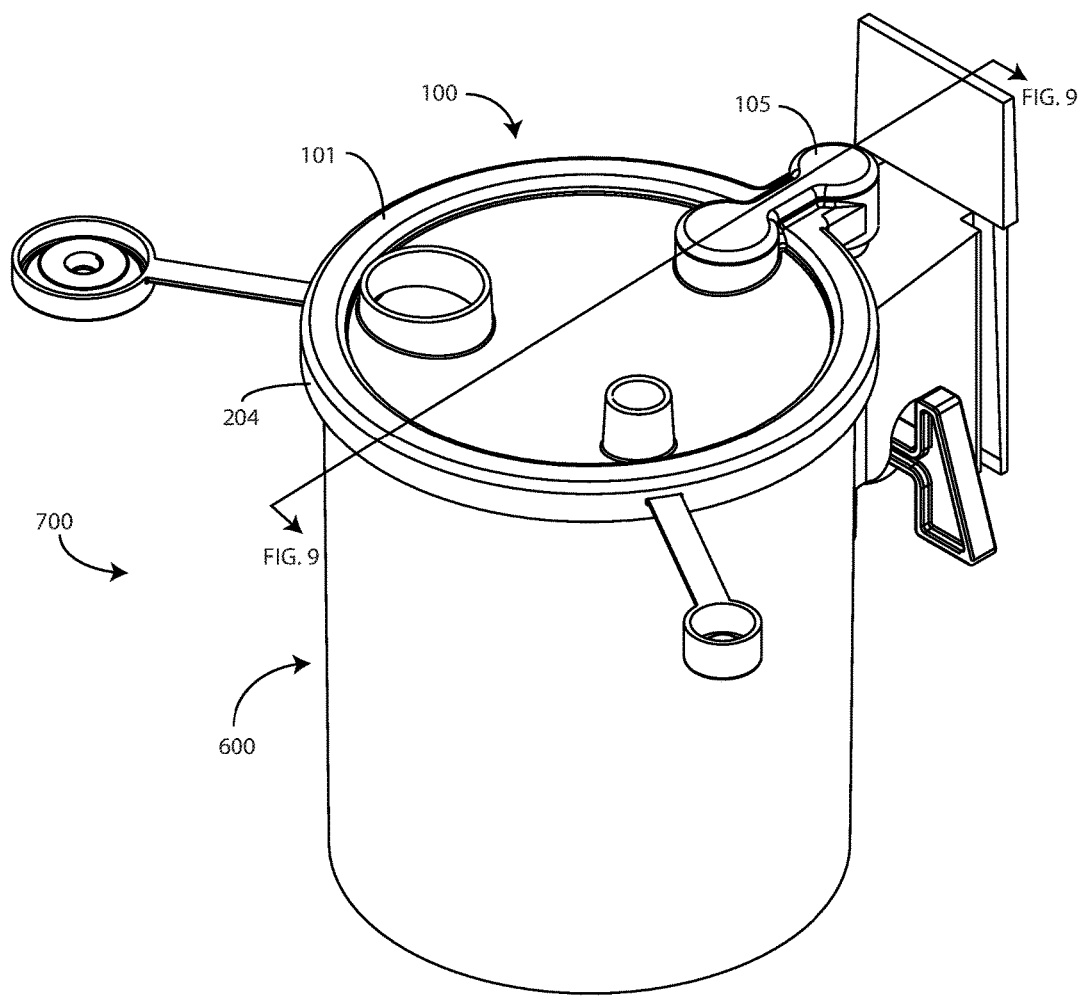
FIG. 8 illustrates one explanatory canister system in accordance with one or more embodiments of the disclosure.

Turning now to FIG. 8, illustrated therein is the assembled canister system 700 once the canister lid 100 has been attached to the lip (602) of the canister 600. In one or more embodiments, the second annular wall 204 of the annular perimeter 101 can include one or more compliant coupling members to attach to the lip (602) of the canister 600. The second annular wall 204 of the annular perimeter 101 can also be configured as cantilevered member operable to "clamp" the second annular wall 204 of the canister lid 100 to the lip (602) of the canister 600. As shown in FIG. 8, the second lobe 106 engages the suction port (606) of the canister 600 when the annular perimeter (101) of the canister lid 100 engages the lip (602) of the canister 600. This is shown in more detail in the sectional view of FIG. 9.

Figure 9:
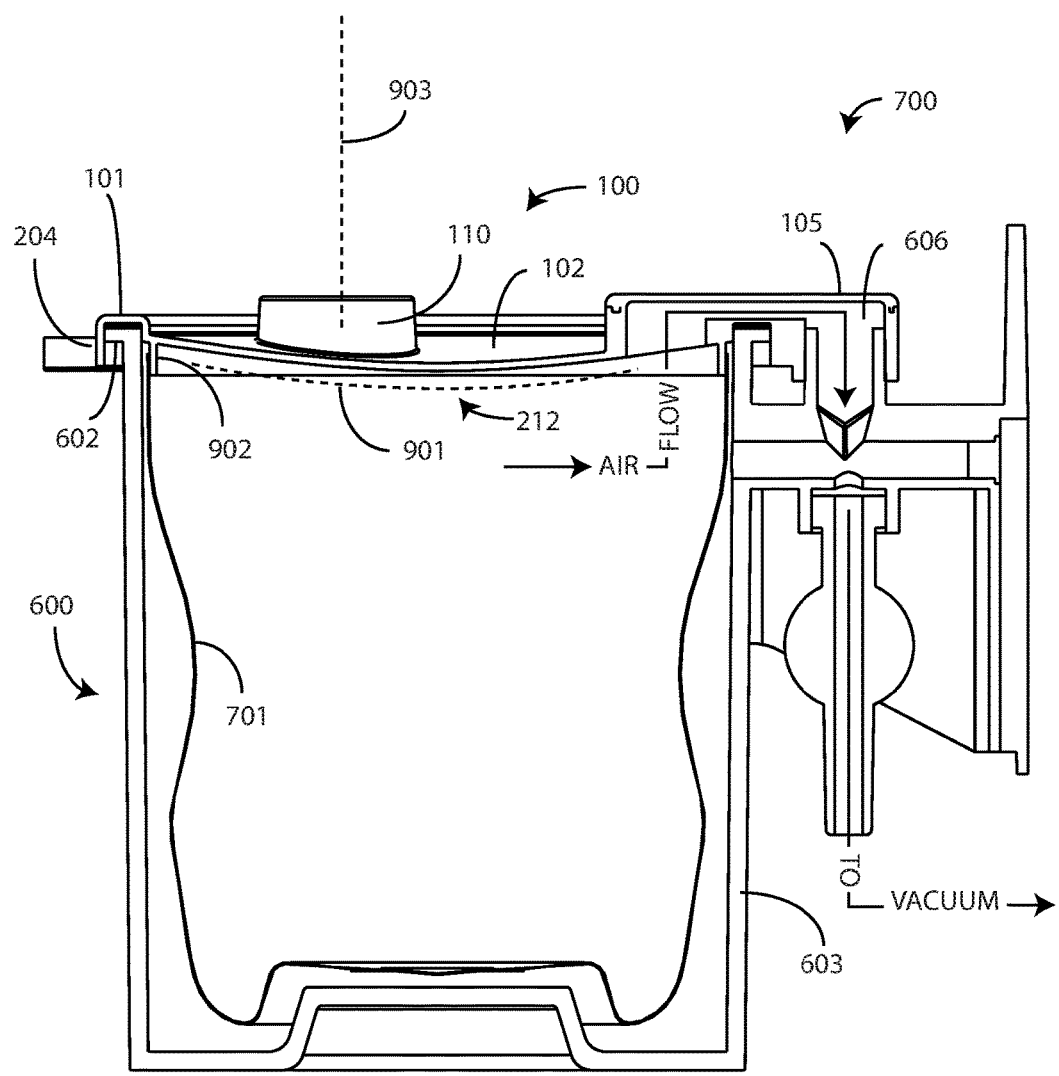
FIG. 9 illustrates a sectional view of one explanatory canister system in accordance with one or more embodiments of the disclosure.

Turning now to FIG. 9, the second lobe 106 of the canister lid 100 is shown engaging the suction port 606 of the canister 600 when the annular perimeter 101 of the canister lid 100 engages the lip 602 of the canister 600.

Other features of the canister lid 100 are visible from this sectional view as well. For example, in this illustrative embodiment the interior portion 102 of the canister lid 100 defines a convex surface 901 toward the container engaging side 212 of the canister lid 100. Additionally, the interior portion 102 is shown spanning an interior of the annular perimeter 101. This convex surface 901 can be advantageous when the pressure within the canister 600 is less than outside the canister 600.

Specifically, when the canister lid 100 is sealed to the canister 600, and pressure is either removed from the exterior of the canister system 700, such as when the suction port 606 is coupled to a vacuum or other suction device, or is added to the interior of the canister 600, such as by fermentation of liquids contained within the canister 600, the convex surface 901 works as a mechanical buttress to improve the seal between the canister lid 100 and canister 600. When the convex surface 901 is pushed outward, the second annular wall 204 of the annular perimeter 101 is pushed inward against the lip 60 of the canister 600, thereby increasing the integrity of the seal therebetween.

In the illustrative embodiment of FIG. 9, the convex surface 901 is configured to extend from the first annular wall 202 of the annular perimeter 101 towards the canister engaging side 212 of the canister lid 100. Said differently, as viewed in FIG. 9, the convex surface 901 points downward, or toward the canister engaging side 212. In one embodiment, the portions of the interior portion 102 defining the sides of the convex surface 901 extend from the first annular wall 202 of the annular perimeter at an angle between ninety-five and one hundred and five degrees. This results in a convex surface 901 shape that is between three and ten millimeters in depth.

Another feature that can be seen in the sectional view of FIG. 9 is a barrier wall 902 extending from the interior portion 102 distally toward the canister engaging side 212 of the canister lid 100. In one or more embodiments, the barrier wall 902 is to engage the disposable liner 701 to ensure that no fluids pass outside the disposable liner into the interior portion of the canister 600 disposed between the disposable liner 701 and the cylindrical sidewall 603.

The orientation of the one or more ports 110,(111) can also be seen in the sectional view of FIG. 9. In this illustrative embodiment, a major axis 903 of the one or more ports 110,(111) is oriented substantially parallel with the barrier wall 902. In other embodiments, the major axis 903 of the one or more ports 110,(111) can be oriented orthogonally with the barrier wall 902 as taught in commonly assigned U.S. patent application Ser. No. 12/769,900, filed Apr. 29, 2010. In still other embodiments, the major axis 903 of the one or more ports 110,(111) can be oriented skew with the barrier wall 902. Other configurations will be obvious to those of ordinary skill in the art having the benefit of this disclosure.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A canister lid, comprising:
   an annular perimeter surrounding an interior portion, the annular perimeter interrupted by a suction conduit defined by a suction duct separating a first lobe and a second lobe, the first lobe disposed interior of the annular perimeter, the second lobe disposed exterior to the annular perimeter, and the suction duct traversing the annular perimeter, the suction conduit comprising a first lobe annular wall, a second lobe annular wall, and one or more suction duct sidewalls;
   a suction conduit cap coupled to each of the first lobe annular wall, the second lobe annular wall, and the one or more suction duct sidewalls; and
   one or more ports extending from the interior portion.

2. The canister lid of claim 1, the one or more ports comprising two ports.

3. The canister lid of claim 2, one port of the two ports comprising a pour spout.

4. The canister lid of claim 3, another port of the two ports comprising a suction port.

5. The canister lid of claim 4, the suction port extending distally away from the interior portion farther than the pour spout.

6. The canister lid of claim 4, further comprising one or more caps to cover the one or more ports on a one-to-one basis, each of the one or more caps coupled to the annular perimeter by a corresponding tab extending from the annular perimeter.

7. The canister lid of claim 4, the first lobe, the pour spout, and the suction port radially separated by about 120 degrees along the interior portion.

8. The canister lid of claim 1, the canister lid comprising a canister engaging side, the interior portion defining a convex surface toward the canister engaging side and spanning an interior of the annular perimeter.

9. The canister lid of claim 1, the annular perimeter defining a canister lip edge receiving recess.

10. The canister lid of claim 9, the canister lip edge receiving recess comprising:
    a first annular wall;
    a second annular wall; and
    a bridge spanning the first annular wall and the second annular wall.

11. The canister lid of claim 10, the canister lid comprising a canister engaging side, further comprising a barrier wall extending from the interior portion distally toward the canister engaging side.

12. The canister lid of claim 11, a major axis of the one or more ports oriented substantially parallel with the barrier wall.

13. The canister lid of claim 1, further comprising a disposable liner attached to the canister lid.

14. The canister lid of claim 1, the first lobe annular wall and the second lobe annular wall having one of a rectangular, triangular, free form, ovular, pentagonal, or hexagonal cross sectional shape.

15. The canister lid of claim 1, the first lobe annular wall and the second lobe annular wall each substantially circular in cross section.

16. The canister lid of claim 13, the first lobe annular wall greater in circumference than the second lobe annular wall.

17. The canister lid of claim 1, further comprising a canister.

18. The canister lid of claim 17, the canister comprising a lip, a sidewall, and a suction port extending distally from the sidewall, the second lobe to engage the suction port when the annular perimeter engages the lip.

* * * * *